(12) United States Patent
Malo Vergara

(10) Patent No.: US 11,541,115 B2
(45) Date of Patent: Jan. 3, 2023

(54) **TRIPLE VACCINE AGAINST *AVIBACTERIUM PARAGALLINARUM* AND AVIAN ENCEPHALOMYELITIS VIRUS AND FOWL POX VIRUS**

(71) Applicant: Boehringer Ingelheim Vetmedica GmbH, Ingelheim am Rhein (DE)

(72) Inventor: Aristoteles Malo Vergara, Panama (PA)

( * ) Notice: Subject to any disclaimer, the term of this patent is extended or adjusted under 35 U.S.C. 154(b) by 0 days.

(21) Appl. No.: 17/104,457

(22) Filed: Nov. 25, 2020

(65) Prior Publication Data
US 2021/0162040 A1    Jun. 3, 2021

(30) Foreign Application Priority Data
Nov. 29, 2019   (EP) .................................. 19212630

(51) Int. Cl.
| | |
|---|---|
| *A61K 39/295* | (2006.01) |
| *A61K 39/102* | (2006.01) |
| *A61K 39/125* | (2006.01) |
| *C12N 7/00* | (2006.01) |
| *A61K 39/275* | (2006.01) |
| *A61P 37/04* | (2006.01) |
| *A61P 31/04* | (2006.01) |
| *A61P 31/14* | (2006.01) |
| *A61P 31/20* | (2006.01) |
| *A61K 39/39* | (2006.01) |
| *A61K 39/00* | (2006.01) |

(52) U.S. Cl.
CPC .......... *A61K 39/295* (2013.01); *A61K 39/102* (2013.01); *A61K 39/125* (2013.01); *A61K 39/275* (2013.01); *A61K 39/39* (2013.01); *A61P 31/04* (2018.01); *A61P 31/14* (2018.01); *A61P 31/20* (2018.01); *A61P 37/04* (2018.01); *C12N 7/00* (2013.01); *A61K 2039/5252* (2013.01); *A61K 2039/5254* (2013.01); *A61K 2039/54* (2013.01); *A61K 2039/545* (2013.01); *A61K 2039/552* (2013.01); *A61K 2039/55566* (2013.01); *C12N 2710/24034* (2013.01); *C12N 2710/24071* (2013.01); *C12N 2770/32034* (2013.01); *C12N 2770/32071* (2013.01)

(58) Field of Classification Search
None
See application file for complete search history.

(56) References Cited

U.S. PATENT DOCUMENTS

| 5,208,023 A | 5/1993 | Nicholas et al. | |
|---|---|---|---|
| 2015/0086590 A1* | 3/2015 | Sakamoto | A61K 39/102 424/214.1 |
| 2021/0162040 A1* | 6/2021 | Malo Vergara | A61K 39/295 |

FOREIGN PATENT DOCUMENTS

JP   515045   2/1976

OTHER PUBLICATIONS

Gong et al. (Veterinary Immunology and Immunopathology. 2014; 158: 3-7).*
El-Zahed et al. (Journal of Veterinary Medical Research. 2010; 20 (1): 126-133).*
Anonymous: "Volvac AE+FP MLV" Lapisa; Jun. 6, 2018, 1 Page.
Sarma G. et al.: "Field safety and efficacy of a unique live virus vaccine for controlling avian encephalomyelitis and fowlpox in poultry", Veterinary World ; vol. 12, No. 8, Aug. 1, 2019, p. 1291-1298.
Blackall P. J.:"Volvac AC Plus", BI Vetmedica; May 16, 2019.
Jacobs A. A. C. et al.:"Efficacy of a trivalent haemophilus paragallinarum vaccine, compared to bivalent vaccines", Veterinary Microbiology; vol. 32, No. 1, Jul. 1, 1992, p. 43-49.
Sharma J. M.: "Introduction to poultry vaccines and immunity"; Advances in Veterinary Medicine; vol. 41; Jan. 1, 1999, p. 481-494.
Blackall P. J. et al.: "Reclassification of Pasteurella gallinarum, [Haemophilus] paragallinarum, Pasteurella avium and Pasteurella volantium . . . ", International Journal of systematic and evolutionary microbiology; vol. 55, No. 1, Oct. 4, 2004, p. 353-362.
Tibor Cserep: "Chapter 5—Vaccines and vaccination", Elsevier Poultry Diseases, Jan. 1, 2008, p. 66-81.
Mockett A. P. A. et al.: "Fowlpox vaccination: Routes of inoculation and pathological effects", Avian Pathology 19: 613-625, 1990.
Diallo I.S. et al.: Field isolates of fowlpox virus contaminated with reticuloendotheliosis virus, Avian Pathology (1998) 27, 60-66.
Ariyoshi R. et al.: "Vaccination against Fowlpox Virus via drinking water", Avian Pathology, 2003, J. Vet. Med. Sci. 65 (10): 1127-1130.
Blackall P. J. et al.: "Proposal of a New Serovar and Altered Nomenclature for Haemophilus paragallinarum in the Kume Hemagglutinin Scheme", Journal of Clinical Microbiology, Jun. 1990, p. 1185-1187.

* cited by examiner

*Primary Examiner* — Shanon A. Foley
(74) *Attorney, Agent, or Firm* — Steffan Finnegan

(57) ABSTRACT

The present invention relates i. a. to an immunogenic composition comprising: a) one or more antigens of *avibacterium paragallinarum* and one or more antigens of avian encephalomyelitis virus and one or more antigens of fowl pox virus; and b) a pharmaceutically acceptable carrier. Furthermore, the present invention relates to methods for immunizing a subject comprising administering to such subject the immunogenic composition of the present invention. Moreover, the present invention relates to methods of treating or preventing clinical signs caused by *avibacterium paragallinarum*, avian encephalomyelitis virus and fowl pox virus in a subject of need, the method comprising administering to the subject a therapeutically effective amount of an immunogenic composition according to the present invention.

14 Claims, 2 Drawing Sheets

PC = positive control; NC = negative control

PC = positive control;  NC = negative control

TRIPLE VACCINE AGAINST *AVIBACTERIUM PARAGALLINARUM* AND AVIAN ENCEPHALOMYELITIS VIRUS AND FOWL POX VIRUS

BACKGROUND OF THE INVENTION

Infectious coryza (IC) is an infectious upper respiratory disease affecting poultry. This disease is caused by *avibacterium paragallinarum*, which was previously known as Haemophilus paragallinarum. Some clinical signs that are commonly seen in IC are rhinitis, facial swelling or edema, anorexia, retarded growth, decreased egg production and some mortality. The disease is very important in the chicken farm industry.

The avian encephalomyelitis virus is a single-stranded RNA (ssRNA) virus belonging to the Picornaviridae family. Infection may cause neurological signs in poultry (such as ataxia, rapid tremor of the head and neck), weakness, weight loss, increased mortality and decreased egg production.

The Fowl pox virus (FPV), a DNA virus of the genus *Avipoxvirus* of the family Poxviridae, infects poultry. Fowl Pox virus diseases have significant economic impact worldwide, with losses resulting from a drop in egg production in layers, reduced growth rates in broilers, blindness, and in some cases death.

However, what is needed are efficacious combination vaccines which provide protection against multiple pathogens. Such combination vaccines are very desirable in order to minimize the number of vaccination handlings required to confer protection against multiple pathogens (animal welfare), to lower administration costs, and to increase acceptance and coverage rates.

However, the problem of interference complicates the development of multi-component vaccines. Specifically, interference refers to the observation that administering multiple antigens often results in a diminished response to certain antigens relative to the immune response observed when such antigens are administered individually. Interference may occur in general when administering multiple antigens. However, in particular, the phenomenon of interference is problematic when combining killed vaccines together with live vaccines since the live vaccine component may be affected by the killed vaccine component (which may comprise a pharmaceutically acceptable carrier).

Thus, there is a need for efficacious combination vaccines which provide protection against multiple pathogens.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an immunogenic composition comprising: a) one or more antigens of *avibacterium paragallinarum* and one or more antigens of avian encephalomyelitis virus and one or more antigens of fowl pox virus; and b) a pharmaceutically acceptable carrier.

Further, the present invention also provides an immunogenic composition comprising: a) one or more antigens of a bacterin of *avibacterium paragallinarum* and one or more antigens of a modified live avian encephalomyelitis virus and one or more antigens of a modified live fowl pox virus; and b) a pharmaceutically acceptable carrier. Thus, the immunogenic composition relates to a combination of a bacterin of *avibacterium paragallinarum* and a modified live avian encephalomyelitis virus and a modified live fowl pox virus.

Furthermore, the present invention also provides an immunogenic composition comprising: a) a bacterin of *avibacterium paragallinarum* and a modified live avian encephalomyelitis virus and a modified live fowl pox virus; and b) a pharmaceutically acceptable carrier.

Moreover, the present invention also provides an immunogenic composition comprising in combination a bacterin of *avibacterium paragallinarum* and a modified live avian encephalomyelitis virus and a modified live fowl pox virus.

Advantageously, the experimental data provided herein clearly provide evidence that the triple vaccine confers protection against avian coryza, avian encephalomyelitis and fowl pox. Surprisingly, no interference with the efficacy of different vaccine components have been detected. There is even a slightly positive synergistic effect, for both the pox vaccine and the AE vaccine efficacy, in the triple vaccine combination which is surprising.

The term "*avibacterium paragallinarum*" is well known to the person skilled in the art. *avibacterium paragallinarum* is a Gram-negative bacterium from the family of Pasteurellaceae. Infectious coryza (IC) is caused by *avibacterium paragallinarum*. Infectious coryza (IC) is an infectious upper respiratory disease affecting poultry.

The term "avian encephalomyelitis virus" is well known to the person skilled in the art. The avian encephalomyelitis virus is a single-stranded RNA (ssRNA) virus belonging to the Picornaviridae family. Infection in poultry may cause neurological signs (such as ataxia, rapid tremor of the head and neck), weakness, weight loss, increased mortality and decreased egg production.

The term "fowl pox virus" is well known to the person skilled in the art. The Fowl pox virus (FPV), a member of the *Avipoxvirus* genus, infects poultry. Fowl Pox virus diseases has significant economic impact worldwide, with losses resulting from a drop in egg production in layers, reduced growth rates in broilers, blindness, and in some cases death.

An "antigen" as used herein refers to, but is not limited to, components which elicit an immunological response in a host to an immunogenic composition or vaccine of interest comprising such antigen or an immunologically active component thereof. The antigen or immunologically active component may be a whole microorganism (in inactivated or modified live form), or any fragment or fraction thereof, which, if administered to a host, can elicit an immunological response in the host. The antigen may be or may comprise complete live organisms in either its original form or as attenuated organisms in a so called modified live vaccine (MLV). The antigen may further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen may comprise whole organisms inactivated by appropriate methods in a so called killed vaccine (KV). If the organism is a bacterium, the killed vaccine is called a bacterin.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of the infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutical response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

In one specific aspect of the immunogenic composition according to the present invention the one or more antigens of avibacterium paragallinarum is a bacterin of avibacterium paragallinarum.

A "bacterin" as used herein refers to an inactivated bacterium. Thus, a bacterin of avibacterium paragallinarum refers to killed, inactivated avibacterium paragallinarum.

In another specific aspect of the immunogenic composition according to the present invention the bacterin of avibacterium paragallinarum is a whole inactivated bacterin of avibacterium paragallinarum.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfate and the alike.

In another specific aspect of the immunogenic composition according to the present invention the bacterin of avibacterium paragallinarum is a whole formalin or thimerosal inactivated bacterin of avibacterium paragallinarum.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the avibacterium paragallinarum. In general, the inactivation process is performed until no growth of the avibacterium paragallinarum can be detected in a suitable cultivation system.

Preferably, the inactivated avibacterium paragallinarum of the present invention is formalin inactivated, preferably using the concentrations as described hereinabove.

Preferred thimerosal inactivation conditions include thimerosal concentration between from about 1% (v/v)-20% (v/v), more preferably from about 3% (v/v)-17% (v/v), even more preferably from about 5% (v/v)-15% (v/v), and most preferably about 8% (v/v)-12% (v/v). Incubation time depends on the resistance of the avibacterium paragallinarum. In general, the inaction process is performed until no growth of the avibacterium paragallinarum can be detected in a suitable cultivation system.

Preferably, the inactivated avibacterium paragallinarum of the present invention is thimerosal inactivated, preferably using the concentrations as described hereinabove.

The inactivated bacterin component of the invention may be incorporated into liposomes using known technology such as that described in Nature, 1974, 252, 252-254 or Journal of Immunology, 1978, 120, 1109-13. In another embodiment of the invention, the inactivated bacterin component of the invention may be conjugated to suitable biological compounds such as polysaccharides, peptides, proteins, or the like, or a combination thereof.

In another specific aspect of the immunogenic composition according to the present invention the fowl pox virus is a modified live fowl pox virus.

In another specific aspect of the immunogenic composition according to the present invention the modified live fowl pox virus is attenuated.

The term "attenuated" refers to a pathogen having a reduced virulence in comparison to the wildtype isolate. In the present invention, an attenuated virus is one in which the virulence has been reduced so that it does not cause clinical signs of that virus infection but is capable of inducing an immune response in the target animal, but may also mean that the clinical signs are reduced in incidence or severity in animals infected with the attenuated virus in comparison with a "control group" of animals infected with non-attenuated virus and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated virus as defined above. Thus, an attenuated, virus strain is one that is suitable for incorporation into an immunogenic composition comprising a modified live virus.

In another specific aspect of the immunogenic composition according to the present invention the modified live fowl pox virus is non-recombinant.

The term "non-recombinant" as used herein relates to a RNA or DNA genome (or RNA sequence, cDNA sequence, DNA sequence or protein) having only modifications that do naturally occur to the corresponding RNA or DNA genome (or RNA sequence, cDNA sequence, DNA sequence or protein).

In another specific aspect of the immunogenic composition according to the present invention the fowl pox virus is recombinant.

The term "recombinant" as used herein relates to a RNA or DNA genome (or RNA sequence, cDNA sequence, DNA sequence or protein) having any modifications that do not naturally occur to the corresponding RNA or DNA genome (or RNA sequence, cDNA sequence, DNA sequence or protein). For instance, a RNA or DNA genome (or RNA sequence, cDNA sequence, DNA sequence or protein) is considered "recombinant" if it contains an insertion, deletion, inversion, relocation or a point mutation introduced artificially, e.g., by human intervention. Therefore, the RNA or DNA genome (or RNA sequence, cDNA sequence, DNA sequence or protein) is not associated with all or a portion of the sequences (RNA, cDNA, DNA sequence or amino acid sequence of the protein) with which it is associated in nature. The term "recombinant" as used with respect to a virus or bacterium, means a virus or bacterium produced by artificial manipulation of the viral or bacterial genome. The term "recombinant virus" or "recombinant bacterium" encompasses genetically modified viruses or bacteria.

Recombinant fowl pox virus vaccines already have ben described in the prior art and have shown to provide protection. Further, such recombinant vaccines against fowl pox are commercially available, exemplarily TROVAC® NDV or TROVAC® H7 subtype (from Boehringer Ingelheim) or VECTORMUNE® FP LT+AE (from Ceva) are based on a modified live fowl pox vaccine.

In another specific aspect of the immunogenic composition according to the present invention the avian encephalomyelitis virus is a modified live avian encephalomyelitis virus.

In another specific aspect of the immunogenic composition according to the present invention the modified live avian encephalomyelitis virus is attenuated.

In another specific aspect of the immunogenic composition according to the present invention the modified live avian encephalomyelitis virus is non-recombinant.

In another specific aspect of the immunogenic composition according to the present invention the avian encephalomyelitis virus is recombinant.

In another specific aspect of the immunogenic composition according to the present invention the immunogenic composition is effective in the treatment and/or prophylaxis of clinical signs caused by *avibacterium paragallinarum* in a subject of need.

The terms "treatment and/or prophylaxis", "clinical signs" and "of need" have been defined elsewhere. The term "infection" or "infected" refer to the infection of a subject by a pathogen, i.e. *avibacterium paragallinarum* or avian encephalomyelitis virus or fowl pox virus.

In another specific aspect of the immunogenic composition according to the present invention the immunogenic composition is effective in the treatment and/or prophylaxis of clinical signs of avian coryza.

In another specific aspect of the immunogenic composition according to the present invention the immunogenic composition is effective in the treatment and/or prophylaxis of clinical signs caused by avian encephalomyelitis virus infection in a subject of need.

In another specific aspect of the immunogenic composition according to the present invention the immunogenic composition is effective in the treatment and/or prophylaxis of clinical signs caused by fowl pox virus infection in a subject of need.

In another specific aspect of the immunogenic composition according to the present invention said subject is avian or poultry. The terms "avian" and "poultry" have been defined elsewhere.

In another specific aspect of the immunogenic composition according to the present invention said immunogenic composition is a vaccine.

The term "vaccine" already has been described elsewhere herein. However, in case where the host displays a protective immunological response such that resistance to new infection will be enhanced and/or the clinical severity of the disease reduced, the immunogenic composition is described as a "vaccine".

In another specific aspect of the immunogenic composition according to the present invention said immunogenic composition is formulated for a single-dose administration.

A single-dose is only administered once. The volume for a single-dose has been defined elsewhere herein.

It has furthermore been shown that one dose of the immunogenic composition of the present invention is effective after the administration of such single dose of such immunogenic composition.

In another specific aspect of the immunogenic composition according to the present invention said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

Preferably, the immunogenic composition further comprises sucrose gelatin stabilizer.

In another specific aspect of the immunogenic composition according to the present invention the immunogenic composition comprises a preservative.

Preferably, formaldehyde (formalin) or thimerosal is used as preservative.

In another specific aspect of the immunogenic composition according to the present invention the immunogenic composition comprises formaldehyde as a preservative.

Preferably, the pharmaceutically acceptable carrier is chitosan. Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In another specific aspect of the immunogenic composition according to the present invention said pharmaceutically acceptable carrier is an adjuvant.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition according to the present invention said pharmaceutically acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from E. coli (recombinant or otherwise), cholera toxin, IMS 1314, muramyl dipeptide, mineral oil, and combinations thereof.

In another specific aspect of the immunogenic composition according to the present invention said pharmaceutically acceptable carrier is an adjuvant selected from the group consisting of mineral oil, water-in-oil emulsion, oil-in-water emulsion, water-in-oil-in-water emulsion, and combinations thereof.

Advantageously, the experimental data provided herein show that water-in-oil emulsion are suitable as adjuvants.

In another specific aspect of the immunogenic composition according to the present invention said pharmaceutically acceptable carrier is a water-in-oil emulsion adjuvant or a water-in-oil emulsion adjuvant comprising a mineral oil. Such water-in-oil emulsion adjuvant or a water-in-oil emulsion adjuvant comprising a mineral oil are well known by the person skilled in the art and are commercially available. Exemplarily, White Mineral Oils are available from Citation™ and Avatech™.

In another specific aspect of the immunogenic composition according to the present invention said mineral oil comprises or consists of saturated aliphatic and alicyclic hydrocarbons. The experimental data provided herein show that mineral oils comprising or consisting of saturated aliphatic and alicyclic hydrocarbons are suitable. However, it has to be understood that other mineral oils will be suitable as well.

In another specific aspect of the immunogenic composition according to the present invention the antigens of avibacterium paragallinarum and avian encephalomyelitis virus and fowl pox virus act synergistically together.

Advantageously, the experimental data provided herein clearly provide evidence that there is no detectable interference with the efficacy of the live attenuated AE (avian encephalomyelitis) and FP (fowl pox) vaccine when combined with the inactivated coryza vaccine (avibacterium paragallinarum) comprising a pharmaceutically acceptable carrier. There is even a slightly positive synergistic effect, for both the pox vaccine and the AE vaccine efficacy, in the triple vaccine combination which is surprising.

The combination of the present invention is advantageous, the combination minimizes the number of immunizations (number of vaccination handlings) required to confer protection against avian coryza, avian encephalomyelitis and fowl pox, it lowers administration costs and increases acceptance and coverage rates.

The term "synergistically" as used herein, means that the immunological response caused by the immunogenic composition of the present invention (triple combination) is increased as compared to a reference monovalent or bivalent immunogenic composition comprising the modified live avian encephalomyelitis virus and/or the modified live fowl pox virus. Preferably, the immunological response is increased by at least 10%, preferably by at least 20%, more preferably by at least 30%, even more preferably by at least 40%, even more preferably by at least 50%, even more preferably by at least 75%, most preferably by at least 100% as compared to said reference monovalent or bivalent immunogenic composition comprising the modified live avian encephalomyelitis virus and/or the modified live fowl pox virus. It is in the general knowledge of a person skilled in the art how to measure the immunological response. In particular, it is clear to such person skilled in the art either to compare the cellular mediated immune response of the immunogenic composition of interest with cellular mediated immune response of the reference, or the antibody mediated immune response of the immunogenic composition of interest with that of the reference composition, but neither the cellular mediated immune response of a immunogenic composition of interest with the antibody mediated immune response of the reference or vice versa. Moreover, the cellular mediated immune response can be measured, for instance, by measuring the activation of cytotoxic T-cells by an immunogenic composition/antigen of interest. The antibody mediated immune response can be measured, for instance, by measuring the amount of antigen specific antibodies, generated in cause of the administration of the immunogenic composition comprising such antigen to an animal. Further, the immunological response can be measured by clinical parameters. Example 1 as described herein describes how to determine the pox lesions or avian encephalomyelitis virus antibody titer (ELISA).

In another specific aspect of the immunogenic composition according to the present invention the immunogenic composition comprises $10^1$ to $10^5$ $EID_{50}$ per dose of the avian encephalomyelitis virus.

In another specific aspect of the immunogenic composition according to the present invention the immunogenic composition comprises $10^1$ to $10^3$ $EID_{50}$ per dose of the avian encephalomyelitis virus.

In another specific aspect of the immunogenic composition according to the present invention the immunogenic composition comprises $10^1$ to $10^5$ $EID_{50}$ per dose of the fowl pox virus.

In another specific aspect of the immunogenic composition according to the present invention the immunogenic composition comprises $10^1$ to $10^3$ $EID_{50}$ per dose of the fowl pox virus.

In another specific aspect of the immunogenic composition according to the present invention the immunogenic composition comprises $10^2$ to $10^{15}$ CFU per dose of the avibacterium paragallinarum before inactivation.

In another specific aspect of the immunogenic composition according to the present invention the immunogenic composition comprises $10^5$ to $10^{10}$ CFU per dose of the avibacterium paragallinarum before inactivation.

Modified live Avian Encephalomyelitis virus vaccines have been intensively described in the prior art. Calnek et al 1961 (Avians Dis 5:297-312) already describe the Calnek vaccine strain and the van Roekel vaccine strain. Further, the Van Roekel strain is deposited with the American Tissue Culture Collection under accession number under or ATCC® VR-2058 (chicken embryo adapted).

Modified live Avian Encephalomyelitis virus vaccines already have been described in the prior art and and have shown to provide protection. Further, such vaccines against Avian Encephalomyelitis virus are commercially available, exemplarily Nobilis® AE 1143 or Nobilis® AE+Pox (from MSD), Volvac® AE+FP MLV (from Boehringer Ingelheim) or Cevac® Tremor L or Cevac® Poximmune AE L (from Ceva).

Further, it is in the general knowledge of a person skilled in the art where to obtain any Avian Encephalomyelitis virus strains. Avian Encephalomyelitis virus strains can be be obtained from scientific Institutes. Furthermore, the Van Roekel strain is deposited with the American Tissue Culture Collection under accession number under ATCC® VR-713 (field strain). Moreover, Avian Encephalomyelitis virus strains can be isolated from the field. The methods to isolate Avian Encephalomyelitis virus strains and to characterize said strains are well known to the person skilled in the art. Moreover, Avian Encephalomyelitis viruses have been sequenced and the genomic sequences are available (exemplarily Marvil et al 1999: J. Gen. Virol. 80: 653-62; or EMBL database accession no. AJ225173). Thus, the virus genome can be generated by synthesizing its sequence and generated upon the application of reverse genetic systems.

By serial passaging of said Avian Encephalomyelitis virus strains modified live vaccines can be easily obtained. This can be done by the person skilled in the art without further ado, however, U.S. Pat. No. 5,208,023 gives further guidance in this respect.

In another specific aspect of the immunogenic composition according to the present invention the Avian Encephalomyelitis virus is selected from a list consisting of: the Calnek 1733 strain and the egg-adapted Van Roekel strain.

In another specific aspect of the immunogenic composition according to the present invention the Avian Encephalomyelitis virus is the Calnek 1733 strain.

Modified live fowl pox vaccines have been intensively described in the prior art. Mocket et al 1990 (Avian Pathology, 19: 613-625) exemplarily describe the modified live HP1 and HP193 fowl pox virus strains, Diallo et al 1998 (Avian Pathology, 27: 60-66) describe the S vaccine strain (FPV30), M vaccine strain (FPV31), steggeles vaccine strain (FPV32, 33 and 34) and Webster's vaccine strain (FPV30) as well as other strains and isolates. Ariyoshi et al 2003 (J.

Vet. Med. Sci. 65(10): 1127-1130) describe the F132-c vaccine strain. Fowl pox vaccine strain Beaudette is deposited with the American Tissue Culture Collection under accession number under ATCC VR-229. The KEM-7 and Gibbs vaccine strain have been described in the prior art as well and are used in commercial available fowl pox vaccines.

Modified live fowl pox vaccines already have been described in the prior art and and have shown to provide protection. Further, such vaccines against fowl pox are commercially available, exemplarily Nobilis® AE+Pox (from MSD), Volvac® AE+FP MLV (from Boehringer Ingelheim) or Cevac® FP L or Cevac® Poximmune AE L (from Ceva).

Further, it is in the general knowledge of a person skilled in the art where to obtain any fowl pox virus strains. Fowl pox strains can be be obtained from scientific Institutes. Furthermore, fowl pox strains can be isolated from the field. The methods to isolate fowl pox strains and to characterize said strains are well known to the person skilled in the art. Moreover, fowl pox viruses have been sequenced and the genomic sequences are available. Thus, the virus genome can be generated by synthesizing its sequence and generated upon the application of reverse genetic systems. By serial passaging of said fowl pox strains modified live vaccines can be easily obtained.

In another specific aspect of the immunogenic composition according to the present invention the Fowl Pox virus is selected from a list consisting of: HP1 and HP193 virus strains, the S vaccine strain (FPV30), the M vaccine strain (FPV31), the steggeles vaccine strains (FPV32, 33 and 34), the Webster's vaccine strain (FPV30), the F132-c vaccine strain, the Beaudette vaccine strain, the KEM-7 vaccine strain and Gibbs vaccine strain.

In another specific aspect of the immunogenic composition according to the present invention the Fowl Pox virus is selected from a list consisting of: the Weybridge vaccine strain, the Beaudette vaccine strain, the KEM-7 vaccine strain and the Gibbs vaccine strain.

In another specific aspect of the immunogenic composition according to the present invention the Fowl Pox virus is the Beaudette vaccine strain.

For *avibacterium paragallinarum* three different serogroupes A, B and C and 9 serovars (A1-A4, B-1 and C1-C4) have been described (Blackall et al 1990; JOURNAL OF CLINICAL MICROBIOLOGY, June 1990, p. 1185-1187). Further, different reference strains have been identified strain 221 (serovar A-A1), strain 2403 (serovar A-A2), strain E-3C (serovar A-A3), strain HP14 (serovar A-A4), strain H-18 (serovar C-C1), strain Modesto (serovar C-C2), strain SA-3 (serovar C-C3), strain HP60 (serovar C-C4) and strain 2671 (serovar B-B1). Further, the *avibacterium paragallinarum* strains are deposited with the American Tissue Culture Collection under accession number under ATCC® 29545, ATCC® 29975 and ATCC® 29976.

Killed *avibacterium paragallinarum* vaccines (exemplarily vaccines comprising serogroups A+B+C or A+C) already have been described in the prior art and and have shown to provide protection. Further, such vaccines against avian coruyza are commercially available, exemplarily Nobilis® Coryza (from MSD), Volvac® AC Plus Bact KV (from Boehringer Ingelheim) or CEVAC® CORYZA K (from Ceva).

Further, it is in the general knowledge of a person skilled in the art where to obtain any *avibacterium paragallinarum* strains. *avibacterium paragallinarum* strains can be be obtained from scientific Institutes. Furthermore, *avibacterium paragallinarum* strains can be isolated from the field. The methods to isolate *avibacterium paragallinarum* strains and to characterize said strains are well known to the person skilled in the art. By inactivation methods (such as by using β-Propiolactone, Thimerosal, Phenol or Formalin) killed vaccines can be easily obtained.

In another specific aspect of the immunogenic composition according to the present invention the *avibacterium paragallinarum* is selected from a list consisting of: serogroup A, serogroup B and serogroup C.

In another specific aspect of the immunogenic composition according to the present invention the *avibacterium paragallinarum* comprises strains of *avibacterium paragallinarum* serogroups A and C.

In another specific aspect of the immunogenic composition according to the present invention the *avibacterium paragallinarum* comprises strains of *avibacterium paragallinarum* serogroups A, B and C.

In another specific aspect of the immunogenic composition according to the present invention the *avibacterium paragallinarum* comprises strains selected from a list consisting of: A1 (O83), B1 (Spross/classical), 4143 (B1 variant), San Francisco 27 (B1 variant) and C2 (Modesto).

In another specific aspect of the immunogenic composition according to the present invention the *avibacterium paragallinarum* comprises the strains A1 (O83), B1 (Spross/classical), 4143 (B1 variant), San Francisco 27 (B1 variant) and C2 (Modesto). Advantageously, it has been shown that the triple combination is effective when comprising such *avibacterium paragallinarum* strains.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for human administration.

Thus, the present invention provides a kit comprising the immunogenic composition as described herein.

In one specific aspect of the kit according to the present invention the bacterin of *avibacterium paragallinarum*, the modified live avian encephalomyelitis virus and the modified live fowl pox virus are in one container.

In one specific aspect of the kit according to the present invention the bacterin of *avibacterium paragallinarum*, the modified live avian encephalomyelitis virus and the modified live fowl pox virus are in one or two container(s).

In one specific aspect of the kit according to the present invention the bacterin of *avibacterium paragallinarum*, the modified live avian encephalomyelitis virus and the modified live fowl pox virus are in separate containers.

In one specific aspect of the kit according to the present invention the bacterin of *avibacterium paragallinarum* is in one container; and the modified live avian encephalomyelitis virus and the modified live fowl pox virus are in one container.

In one specific aspect of the kit according to the present invention the kit further comprises an instruction letter for the treatment and/or prophylaxis of diseases of avians.

In one specific aspect of the kit according to the present invention the kit further comprises an instruction letter for the treatment and/or prophylaxis of diseases of poultry.

In one specific aspect of the kit according to the present invention the kit further comprises an instruction letter for the treatment and/or prophylaxis of avian coryza and/or avian encephalomyelitis virus and/or fowl pox virus.

In another specific aspect of the kit according to the present invention the kit further comprises a dispenser capable of administering a vaccine to an animal, avian or poultry.

Moreover, according to a further aspect, said instruction letter comprises the information of a repeatable administration of at least one dose of said combination vaccines.

Method of Treatments

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular infection in a flock or in the reduction in the severity of clinical signs caused by or associated with the particular infection.

Further, the immunization of a subject in need with the immunogenic compositions as provided herewith, results in preventing infection of a subject by the particular infection. Even more preferably, immunization results in an effective, long-lasting, immunological-response against the particular infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with the particular infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected (with *avibacterium paragallinarum* and/or avian encephalomyelitis virus and/or fowl pox virus).

Further, the present invention provides a method of treating or preventing clinical signs caused by avian encephalomyelitis virus in a subject of need, the method comprising administering to the subject a therapeutically effective amount of an immunogenic composition as described herein.

Further, the present invention provides a method of treating or preventing clinical signs caused by fowl pox virus in a subject of need, the method comprising administering to the subject a therapeutically effective amount of an immunogenic composition as described herein.

Further, the present invention provides a method of treating or preventing clinical signs caused by fowl pox virus and avian encephalomyelitis virus in a subject of need, the method comprising administering to the subject a therapeutically effective amount of an immunogenic as described herein.

Further, the present invention provides a method of treating or preventing clinical signs caused by *avibacterium paragallinarum* in a subject of need, the method comprising administering to the subject a therapeutically effective amount of an immunogenic composition as described herein.

Further, the present invention provides a method of treating or preventing clinical signs caused by fowl pox virus and avian encephalomyelitis virus and *avibacterium paragallinarum* in a subject of need, the method comprising administering to the subject a therapeutically effective amount of an immunogenic composition as described herein.

The term "treating or preventing" refers to the lessening of the incidence of the particular infection (with *avibacterium paragallinarum* and/or avian encephalomyelitis virus and/or fowl pox virus) in a flock or the reduction in the severity of clinical signs caused by or associated with the particular infection. Thus, the term "treating or preventing" also refers to the reduction of the number of subjects in a flock that become infected (=lessening of the incidence of the particular infection) or to the reduction of the severity of clinical signs normally associated with or caused by the particular infection or the reduction of virus shedding after infection or preventing or lessening egg drop in laying hens after infection in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected and wherein such subjects already show some clinical signs caused by or associated with such infection. The term "prophylaxis" refers to the administration of a subject prior to any infection of such subject or at least where such subject or none of the subjects in a group of subjects do not show any clinical signs caused by or associated with the infection. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular infection in a flock or to reduce the severity of clinical signs of the particular infection (with *avibacterium paragallinarum* and/or avian encephalomyelitis virus and/or fowl pox virus).

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected.

The term "clinical signs" as used herein refers to signs of infection of a subject from *avibacterium paragallinarum* and/or avian encephalomyelitis virus and/or fowl pox virus. The clinical signs of infection depend on the pathogen selected.

Examples for such clinical signs caused by infection with *avibacterium paragallinarum* include but are not limited to rhinitis, facial swelling or edema, anorexia, reduced growth rates, decreased egg production, lethargy and increased mortality.

Examples for such clinical signs caused by infection with avian encephalomyelitis virus include but are not limited ataxia, rapid tremor of the head and neck, weakness, weight loss, increased mortality and decreased egg production.

Examples for such clinical signs caused by infection with fowl pox virus include but are not limited to pox; spreading eruptions, scabs and lesions on comb and wattles; lesions in the mouth, pharynx, larynx and trachea; a decreased egg production; reduced growth rates; blindness; and increased mortality.

The clinical signs include but are not limited to clinical signs that are directly observable from a live animal. Examples for clinical signs that are directly observable from a live animal include pox; eruptions, scabs and lesions on comb and wattles; lesions in the mouth, pharynx, larynx and trachea; ruffled feathers; weight loss; reduced growth rates; reduced appetite; lameness; lethargy; wasting and unthriftiness and the like.

Preferably, the clinical signs lessened in incidence or severity in a treated subject compared to subjects that are either not treated or treated with an immunogenic composition that was available prior to the present invention but subsequently infected refer to a shorter duration of bacteremia, shorter duration of viremia, a lower bacterial load, a lower viral load, reduced mortality, reduced tremors, reduced ataxia, reduced weakness, reduced weight loss, reduced drop in egg production, reduced lesions, reduced anorexia, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the mortality in a subject of need, in comparison to a subject of a non-immunized control group of the same species, the method comprising administering to the subject a therapeutically effective amount of an immunogenic composition as described herein.

Further, the present invention provides a method of reducing the tremors in a subject of need, in comparison to a subject of a non-immunized control group of the same species, the method comprising administering to the subject a therapeutically effective amount of an immunogenic composition as described herein.

Further, the present invention provides a method of reducing the drop in egg production in a subject of need, in comparison to a subject of a non-immunized control group of the same species, the method comprising administering to the subject a therapeutically effective amount of an immunogenic composition as described herein.

Further, the present invention provides a method of reducing the pox or pox lesions in a subject of need, in comparison to a subject of a non-immunized control group of the same species, the method comprising administering to the subject a therapeutically effective amount of an immunogenic composition as described herein.

As shown in the Examples, the immunogenic composition as provided herein has been proven to be efficacious for treating and preventing fowl pox virus and avian encephalomyelitis virus infections and is also efficacious for treating and preventing *avibacterium paragallinarum* infections.

The term "reducing" or or "reduced" or "reduction" or lower" are used interchangeable in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected.

The term "reduction of mortality, tremors, drop in egg production, pox or pox lesions" means, that said clinical sign is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure said clinical signs/parameters.

In one aspect of the present invention said subject is avian.

The term "avian" is well known to the person skilled in the art. The term "avian" encompasses all birds including poultry.

In one aspect of the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one aspect of the present invention said subject is selected from the list consisting of chicken, turkey, quail, or pheasant.

In one aspect of the present invention said subject is chicken.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

The vaccine for intramuscular or subcutaneous vaccination may contain the dose in a volume of 30 μl to 1000 μl.

Preferably, the single-dose has a total volume between about 30 μl and 1000 μl, more preferably between about 100 μl and 800 μl, more preferably between about 100 μl, 200 μl and 700 μl with a single 200 μl, 300 μl, 4000 μl, 500 μl, 600 μl, 700 μl or 800 μl dose being the most preferred.

In one aspect of the present invention the immunogenic composition is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitoneally, intrathecally, intratracheally, intracutaneously, intracardially, intralobally, intralobarly, intramedullary, intrapulmonarily, intrarectally, and intravaginally. However, most preferred the immunogenic composition is administered subcutaneously, intramuscularly, oral, in ovo, via spray, via drinking water or by eye drop.

In one aspect of the present invention said immunogenic composition is administered subcutaneously, intramuscularly, intracutaneously, oral or by eye drop.

In one aspect of the present invention said immunogenic composition is administered subcutaneously intramuscularly.

Typically, the vaccine comprise the avian encephalomyelitis virus in a concentration of $10^1$ to $10^8$ $EID_{50}$ (50% Egg Infective Dose) per dose, preferably in a concentration of $10^1$ to $10^5$ $EID_{50}$ per dose and, more preferably, in a concentration of $10^1$ to $10^3$ $EID_{50}$ per dose.

In one aspect of the present invention the immunogenic composition comprises $10^1$ to $10^5$ $EID_{50}$ per dose of the avian encephalomyelitis virus.

In one aspect of the present invention the immunogenic composition comprises $10^1$ to $10^3$ $EID_{50}$ per dose of the avian encephalomyelitis virus.

Typically, the vaccine comprise the fowl pox virus in a concentration of $10^1$ to $10^8$ $EID_{50}$ (50% Egg Infective Dose) per dose, preferably in a concentration of $10^1$ to $10^5$ $EID_{50}$ per dose and, more preferably, in a concentration of $10^1$ to $10^3$ $EID_{50}$ per dose.

In one aspect of the present invention the immunogenic composition comprises $10^1$ to $10^5$ $EID_{50}$ per dose of the fowl pox virus.

In one aspect of the present invention the immunogenic composition comprises $10^1$ to $10^3$ $EID_{50}$ per dose of the fowl pox virus.

Typically, the vaccine comprise the *avibacterium paragallinarum* in a concentration of $10^1$ to $10^{20}$ CFU (colony forming unit) per dose before inactivation, preferably in a concentration of $10^2$ to $10^{15}$ $EID_{50}$ per dose and, more preferably, in a concentration of $10^5$ to $10^{10}$ $EID_{50}$ per dose.

In one aspect of the present invention the immunogenic composition comprises $10^2$ to $10^{15}$ CFU per dose of the *avibacterium paragallinarum* before inactivation.

In one aspect of the present invention the immunogenic composition comprises $10^5$ to $10^{10}$ CFU per dose of the *avibacterium paragallinarum* before inactivation.

In one aspect of the present invention the immunogenic composition comprises $10^2$ to $10^3$ $EID_{50}$ per dose of the avian encephalomyelitis virus, $10^2$ to $10^3$ $EID_{50}$ per dose of the fowl pox virus and $10^7$ to $10^9$ CFU per dose of the *avibacterium paragallinarum* before inactivation.

In one aspect of the present invention the immunogenic composition is administered to subjects from 2 weeks of age onwards, 3 weeks of age onwards, 4 weeks of age onwards, 6 weeks of age onwards or 8 weeks of age onwards.

In one aspect of the present invention the immunogenic composition is administered to subjects from 2 weeks of age onwards.

In one aspect of the present invention the immunogenic composition is administered to subjects from 3 weeks of age onwards.

In one aspect of the present invention the immunogenic composition is administered to subjects from 6 weeks of age onwards.

In one aspect of the present invention the immunogenic composition is administered to subjects 5 to 8 weeks before the onset of lay.

In one aspect of the present invention the immunogenic composition is administered to subjects from 3 weeks of age onwards.

As shown in the Examples the immunogenic composition as provided herein has been proven to be safe and efficacious when administered to 3 week old poultry.

In one aspect of the present invention said method results in an improvement in an efficacy parameter selected from the group consisting of: shorter duration of bacteremia, shorter duration of viremia, a lower bacterial load, a lower viral load, reduced mortality, reduced tremors, reduced ataxia, reduced weakness, reduced weight loss, reduced drop in egg production, reduced lesions, reduced anorexia or combinations thereof, in comparison to a subject of a non-immunized control group of the same species.

The terms "virus load" or "bacterial load" is well known to the person skilled in that art. The term virus load (bacterial load) is interchangeable used with the term viral titer (bacterial titer) herein. The virus load (bacterial load) or virus titer (bacterial titer) is a measure of the severity of an active viral (bacterial) infection, and can be determined by methods known to the person skilled in the art. The determination can be based on the detection of viral (bacterial) proteins such as by antibody binding to the viral (bacterial) proteins and further detection or, alternatively, by detection of viral (bacterial) RNA by amplification methods such as RT-PCR. Exemplary, the virus load (bacterial load) or virus titer (bacterial titer) can be calculated by estimating the live amount of virus (bacteria) in an involved body fluid such as a number of RNA copies per milliliter of blood plasma.

The term "reducing", "reduced", "reduction" or "lower" or "shorter" means, that the efficacy parameter (duration of bacteremia, duration of viremia, bacterial load, viral load, mortality, tremors, ataxia, weakness, weight loss, drop in egg production, lesions, anorexia) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

In one aspect of the present invention the treatment or prevention results in a prevention or reduced mortality as compared to subjects of a non-treated control group of the same species.

In one aspect of the present invention the treatment or prevention results in a prevention or reduced tremors as compared to subjects of a non-treated control group of the same species.

In one aspect of the present invention the treatment or prevention results in a prevention or reduced drop in egg production as compared to subjects of a non-treated control group of the same species.

In one aspect of the present invention the treatment or prevention results in a prevention or reduced pox or pox lesions as compared to subjects of a non-treated control group of the same species.

The present invention further provides an immunogenic composition comprising in combination:
a bacterin of *avibacterium paragallinarum*, and
a modified live avian encephalomyelitis virus, and
a modified live fowl pox virus; and
a water-in-oil emulsion adjuvant or a water-in-oil emulsion adjuvant comprising a mineral oil.

The present invention further provides an immunogenic composition comprising in combination:
a bacterin of *avibacterium paragallinarum* with $10^5$ to $10^{10}$ CFU per dose of the *avibacterium paragallinarum* before inactivation, and
a modified live avian encephalomyelitis virus with $10^1$ to $10^3$ $EID_{50}$ per dose of the avian encephalomyelitis virus, and
a modified live fowl pox virus $10^1$ to $10^3$ $EID_{50}$ per dose of the fowl pox virus; and
a water-in-oil emulsion adjuvant or a water-in-oil emulsion adjuvant comprising a mineral oil.

The present invention further provides an immunogenic composition comprising in combination:
a bacterin of *avibacterium paragallinarum*, and
a modified live avian encephalomyelitis virus, and
a modified live fowl pox virus; and
a water-in-oil emulsion adjuvant comprising a mineral oil comprising or consisting of saturated aliphatic and alicyclic hydrocarbons.

The present invention further provides an immunogenic composition comprising in combination:
a bacterin of *avibacterium paragallinarum* with $10^5$ to $10^{10}$ $EID_{50}$ per dose of the *avibacterium paragallinarum* before inactivation, and
a modified live avian encephalomyelitis virus with $10^1$ to $10^3$ $EID_{50}$ per dose of the avian encephalomyelitis virus, and
a modified live fowl pox virus $10^1$ to $10^3$ $EID_{50}$ per dose of the fowl pox virus; and
a water-in-oil emulsion adjuvant comprising a mineral oil comprising or consisting of saturated aliphatic and alicyclic hydrocarbons.

In one aspect of the present invention said immunogenic composition is a vaccine.

In one aspect of the present invention said immunogenic composition comprises $10^2$ to $10^3$ $EID_{50}$ per dose of the avian encephalomyelitis virus.

In one aspect of the present invention said immunogenic composition comprises $10^2$ to $10^3$ $EID_{50}$ per dose of the fowl pox virus.

In one aspect of the present invention said immunogenic composition comprises $10^7$ to $10^9$ CFU per dose of the *avibacterium paragallinarum* before inactivation.

The present invention further provides an immunogenic composition as described herein for therapeutic use.

The present invention further provides an immunogenic composition as described herein for use as an immunogen or vaccine.

The present invention further provides an immunogenic composition as described herein for use as a medicament.

The present invention further provides the use of the immunogenic composition as described herein for the manufacture of a medicament.

The present invention further provides a method of preparing an immunogenic composition comprising:
a.) providing a bacterin of *avibacterium paragallinarum*; and
b.) providing a modified live avian encephalomyelitis virus; and
c.) providing a modified live fowl pox virus;
d.) combining the components of a) to c) to have a trivalent composition; and
e.) obtaining said trivalent composition; and
f.) addition of a pharmaceutically acceptable carrier.

The term "obtaining" may comprise harvest, isolation, purification and/or formulation (e.g. finishing and/or blending).

In one specific aspect of the method of preparing the immunogenic composition according to the present invention said pharmaceutically acceptable carrier is an adjuvant.

In another specific aspect of the method of preparing the immunogenic composition according to the present invention said pharmaceutically acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from *E. coli* (recombinant or otherwise), cholera toxin, IMS 1314, muramyl dipeptide, mineral oil, and combinations thereof.

In another specific aspect of the method of preparing the immunogenic composition according to the present invention said pharmaceutically acceptable carrier is an adjuvant selected from the group consisting of mineral oil, water-in-oil emulsion, oil-in-water emulsion, water-in-oil-in-water emulsion, and combinations thereof.

In another specific aspect of the method of preparing the immunogenic composition according to the present invention said pharmaceutically acceptable carrier is a water-in-oil emulsion adjuvant or a water-in-oil emulsion adjuvant comprising a mineral oil.

In another specific aspect of the method of preparing the immunogenic composition according to the present invention said mineral oil comprises or consists of saturated aliphatic and alicyclic hydrocarbons.

In another specific aspect of the method of preparing the immunogenic composition according to the present invention the immunogenic composition comprises $10^1$ to $10^5$ $EID_{50}$ per dose of the avian encephalomyelitis virus.

In another specific aspect of the method of preparing the immunogenic composition according to the present invention the immunogenic composition comprises $10^1$ to $10^5$ $EID_{50}$ per dose of the avian encephalomyelitis virus.

In another specific aspect of the method of preparing the immunogenic composition according to the present invention the immunogenic composition comprises $10^1$ to $10^5$ $EID_{50}$ per dose of the fowl pox virus.

In another specific aspect of the method of preparing the immunogenic composition according to the present invention the immunogenic composition comprises $10^1$ to $10^3$ $EID_{50}$ per dose of the fowl pox virus.

In another specific aspect of the method of preparing the immunogenic composition according to the present invention the immunogenic composition comprises $10^2$ to $10^{15}$ CFU per dose of the *avibacterium paragallinarum* before inactivation.

In another specific aspect of the method of preparing the immunogenic composition according to the present invention the immunogenic composition comprises $10^5$ to $10^{10}$ CFU per dose of the *avibacterium paragallinarum* before inactivation.

CLAUSES

The following clauses are also described herein:
1. An immunogenic composition comprising: a) one or more antigens of *avibacterium paragallinarum* and one or more antigens of avian encephalomyelitis virus and one or more antigens of fowl pox virus; and b) a pharmaceutically acceptable carrier.
2. An immunogenic composition comprising: a) one or more antigens of a bacterin of *avibacterium paragallinarum* and one or more antigens of a modified live avian encephalomyelitis virus and one or more antigens of a modified live fowl pox virus; and b) a pharmaceutically acceptable carrier.
3. An immunogenic composition comprising: a) a bacterin of *avibacterium paragallinarum* and a modified live avian encephalomyelitis virus and a modified live fowl pox virus; and b) a pharmaceutically acceptable carrier.
4. An immunogenic composition comprising in combination a bacterin of *avibacterium paragallinarum* and a modified live avian encephalomyelitis virus and a modified live fowl pox virus.
5. The immunogenic composition of clause 1, wherein the one or more antigens of *avibacterium paragallinarum* is a bacterin of *avibacterium paragallinarum*.
6. The immunogenic composition of any one of clauses 2 to 5, wherein the bacterin of *avibacterium paragallinarum* is a whole inactivated bacterin of *avibacterium paragallinarum*.
7. The immunogenic composition of any one of clauses 2 to 6, wherein the bacterin of *avibacterium paragallinarum* is a whole formalin or thimerosal inactivated bacterin of *avibacterium paragallinarum*
8. The immunogenic composition of clause 1, wherein the fowl pox virus is a modified live fowl pox virus.
9. The immunogenic composition of any one of clauses 2 to 4 and 6 to 8, wherein the modified live fowl pox virus is attenuated.
10. The immunogenic composition of any one of clauses 2 to 4 and 6 to 9, wherein the modified live fowl pox virus is non-recombinant.
11. The immunogenic composition of any one of clauses 2 to 4 and 6 to 9, wherein the modified live fowl pox virus is recombinant.
12. The immunogenic composition of clause 1, wherein the avian encephalomyelitis virus is a modified live avian encephalomyelitis virus.
13. The immunogenic composition of clauses 2 to 4 and 6 to 12, wherein the modified live avian encephalomyelitis virus is attenuated.
14. The immunogenic composition of any one of clauses 2 to 4 and 6 to 13, wherein the modified live avian encephalomyelitis virus is non-recombinant.
15. The immunogenic composition of any one of clauses 2 to 4 and 6 to 13, wherein the modified live avian encephalomyelitis virus is recombinant.
16. The immunogenic composition of any one of clauses 1 to 15, wherein the immunogenic composition is effective in the treatment and/or prophylaxis of clinical signs caused by *avibacterium paragallinarum* infection in a subject of need.
17. The immunogenic composition of any one of clauses 1 to 16, wherein the immunogenic composition is effective in the treatment and/or prophylaxis of clinical signs of avian coryza.
18. The immunogenic composition of any one of clauses 1 to 17, wherein the immunogenic composition is effective in the treatment and/or prophylaxis of clinical signs caused by avian encephalomyelitis virus infection in a subject of need.
19. The immunogenic composition of any one of clauses 1 to 18, wherein the immunogenic composition is effective in the treatment and/or prophylaxis of clinical signs caused by fowl pox virus infection in a subject of need.
20. The immunogenic composition of any one of clauses 16 to 19, wherein said subject is avian or poultry.
21. The immunogenic composition of any one of clauses 1 to 20, wherein said immunogenic composition is a vaccine.
22. The immunogenic composition of any one of clauses 1 to 21, wherein said immunogenic composition is formulated for a single-dose administration.
23. The immunogenic composition of any one of clauses 1 to 3 and 5 to 19, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.
24. The immunogenic composition of any one of clauses 1 to 23, wherein the immunogenic composition comprises a preservative.
25. The immunogenic composition of any one of clauses 1 to 24, wherein the immunogenic composition comprises formaldehyde as a preservative.
26. The immunogenic composition of any one of clauses 1 to 3 and 5 to 25, wherein said pharmaceutically acceptable carrier is an adjuvant.
27. The immunogenic composition of any one of clauses 1 to 3 and 5 to 26, wherein said pharmaceutically acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from *E. coli* (recombinant or otherwise), cholera toxin, IMS 1314, muramyl dipeptide, mineral oil, and combinations thereof.
28. The immunogenic composition of any one of clauses 1 to 3 and 5 to 27, wherein said pharmaceutically acceptable carrier is an adjuvant selected from the group consisting of mineral oil, water-in-oil emulsion, oil-in-water emulsion, water-in-oil-in-water emulsion, and combinations thereof.

29. The immunogenic composition of any one of clauses 1 to 3 and 5 to 28, wherein said pharmaceutically acceptable carrier is a water-in-oil emulsion adjuvant or a water-in-oil emulsion adjuvant comprising a mineral oil.

30. The immunogenic composition of any one of clauses 27 to 29, wherein said mineral oil comprises or consists of saturated aliphatic and alicyclic hydrocarbons.

31. The immunogenic composition of any one of clauses 1 to 30, wherein the antigens of *avibacterium paragallinarum* and avian encephalomyelitis virus and fowl pox virus act synergistically together.

32. The immunogenic composition of any one of clauses 1 to 31, wherein the immunogenic composition comprises $10^1$ to $10^5$ $EID_{50}$ per dose of the avian encephalomyelitis virus.

33. The immunogenic composition of any one of clauses 1 to 32, wherein the immunogenic composition comprises $10^1$ to $10^3$ $EID_{50}$ per dose of the avian encephalomyelitis virus.

34. The immunogenic composition of any one of clauses 1 to 33, wherein the immunogenic composition comprises $10^1$ to $10^5$ $EID_{50}$ per dose of the fowl pox virus.

35. The immunogenic composition of any one of clauses 1 to 34, wherein the immunogenic composition comprises $10^1$ to $10^3$ $EID_{50}$ per dose of the fowl pox virus.

36. The immunogenic composition of any one of clauses 1 to 35, wherein the immunogenic composition comprises $10^2$ to $10^{15}$ CFU per dose of the *avibacterium paragallinarum* before inactivation.

37. The immunogenic composition of any one of clauses 1 to 36, wherein the immunogenic composition comprises $10^5$ to $10^{10}$ CFU per dose of the *avibacterium paragallinarum* before inactivation.

38. The immunogenic composition of any one of clauses 1 to 37, wherein the Avian Encephalomyelitis virus is selected from a list consisting of: the Calnek 1733 strain and the egg-adapted Van Roekel strain.

39. The immunogenic composition of any one of clauses 1 to 38, wherein the Avian Encephalomyelitis virus is the Calnek 1733 strain.

40. The immunogenic composition of any one of clauses 1 to 39, wherein the Fowl Pox virus is selected from a list consisting of: HP1 and HP193 virus strains, the S vaccine strain (FPV30), the M vaccine strain (FPV31), the steggeles vaccine strains (FPV32, 33 and 34), the Webster's vaccine strain (FPV30), the F132-c vaccine strain, the Beaudette vaccine strain, the KEM-7 vaccine strain and Gibbs vaccine strain.

41. The immunogenic composition of any one of clauses 1 to 40, wherein the Fowl Pox virus is selected from a list consisting of: the Weybridge vaccine strain, the Beaudette vaccine strain, the KEM-7 vaccine strain and the Gibbs vaccine strain.

42. The immunogenic composition of any one of clauses 1 to 41, wherein the Fowl Pox virus is the Beaudette vaccine strain.

43. The immunogenic composition of any one of clauses 1 to 42, wherein the *avibacterium paragallinarum* is selected from a list consisting of: serogroup A, serogroup B and serogroup C.

44. The immunogenic composition of any one of clauses 1 to 43, wherein the *avibacterium paragallinarum* comprises strains of *avibacterium paragallinarum* serogroups A and C.

45. The immunogenic composition of any one of clauses 1 to 44, wherein the *avibacterium paragallinarum* comprises strains of *avibacterium paragallinarum* serogroups A, B and C.

46. The immunogenic composition of any one of clauses 1 to 45, wherein the *avibacterium paragallinarum* comprises strains selected from a list consisting of: A1 (O83), B1 (Spross/classical), 4143 (B1 variant) San Francisco 27 (B1 variant) and C2 (Modesto).

47. The immunogenic composition of any one of clauses 1 to 46, wherein the *avibacterium paragallinarum* comprises the strains A1 (O83), B1 (Spross/classical), 4143 (B1 variant), San Francisco 27 (B1 variant) and C2 (Modesto).

48. A kit comprising the immunogenic composition of any one of clauses 1 to 47.

49. The kit according to clause 48, wherein the bacterin of *avibacterium paragallinarum*, the modified live avian encephalomyelitis virus and the modified live fowl pox virus are in one container.

50. The kit according to clause 48, wherein the bacterin of *avibacterium paragallinarum*, the modified live avian encephalomyelitis virus and the modified live fowl pox virus are in one or two container(s).

51. The kit according to clause 48, wherein the bacterin of *avibacterium paragallinarum*, the modified live avian encephalomyelitis virus and the modified live fowl pox virus are in separate containers.

52. The kit according to clause 48, wherein the bacterin of *avibacterium paragallinarum* is in one container; and the modified live avian encephalomyelitis virus and the modified live fowl pox virus are in one container.

53. The kit according to anyone of clauses 48 to 52, wherein the kit further comprises an instruction letter for the treatment and/or prophylaxis of diseases of avians.

54. The kit according to anyone of clauses 48 to 53, wherein the kit further comprises an instruction letter for the treatment and/or prophylaxis of diseases of poultry.

55. The kit according to anyone of clauses 48 to 54, wherein the kit further comprises an instruction letter for the treatment and/or prophylaxis of avian coryza and/or avian encephalomyelitis virus and/or fowl pox virus.

56. A method for immunizing a subject comprising administering to such subject an immunogenic composition of any one of clauses 1 to 47.

57. A method of treating or preventing clinical signs caused by avian encephalomyelitis virus in a subject of need, the method comprising administering to the subject a therapeutically effective amount of an immunogenic composition according to any one of clauses 1 to 47.

58. A method of treating or preventing clinical signs caused by fowl pox virus in a subject of need, the method comprising administering to the subject a therapeutically effective amount of an immunogenic composition according to any one of clauses 1 to 47.

59. A method of treating or preventing clinical signs caused by fowl pox virus and avian encephalomyelitis virus in a subject of need, the method comprising administering to the subject a therapeutically effective amount of an immunogenic composition according to any one of clauses 1 to 47.

60. A method of treating or preventing clinical signs caused by *avibacterium paragallinarum* in a subject of need, the method comprising administering to the subject a therapeutically effective amount of an immunogenic composition according to any one of clauses 1 to 47.

61. A method of treating or preventing clinical signs caused by fowl pox virus and avian encephalomyelitis virus and *avibacterium paragallinarum* in a subject of need, the method comprising administering to the subject a therapeutically effective amount of an immunogenic composition according to any one of clauses 1 to 47.

62. A method of reducing the mortality in a subject of need, in comparison to a subject of a non-immunized control group of the same species, the method comprising administering to the subject a therapeutically effective amount of an immunogenic composition according to any one of clauses 1 to 47.

63. A method of reducing the tremors in a subject of need, in comparison to a subject of a non-immunized control group of the same species, the method comprising administering to the subject a therapeutically effective amount of an immunogenic composition according to any one of clauses 1 to 47.

64. A method of reducing the drop in egg production in a subject of need, in comparison to a subject of a non-immunized control group of the same species, the method comprising administering to the subject a therapeutically effective amount of an immunogenic composition according to any one of clauses 1 to 47.

65. A method of reducing the pox or pox lesions in a subject of need, in comparison to a subject of a non-immunized control group of the same species, the method comprising administering to the subject a therapeutically effective amount of an immunogenic composition according to any one of clauses 1 to 47.

66. The immunogenic composition according to any one of clauses 1 to 47 for use in a method for immunizing a subject, the method comprising administering to the subject a therapeutically effective amount of said immunogenic composition.

67. The immunogenic composition according to any one of clauses 1 to 47 for use in a method of treating or preventing clinical signs caused by fowl pox virus and/or avian encephalomyelitis virus and/or *avibacterium paragallinarum* in a subject of need, the method comprising administering to the subject a therapeutically effective amount of said immunogenic composition.

68. The immunogenic composition according to any one of clauses 1 to 47 for use in a method of reducing the mortality and/or the tremors and/or the drop in egg production and/or pox or pox lesions in a subject of need, in comparison to a subject of a non-immunized control group of the same species, the method comprising administering to the subject a therapeutically effective amount of said immunogenic composition.

69. The method or use of any one of clauses 56 to 68, wherein said subject is avian.

70. The method or use of any one of clauses 56 to 69, wherein said subject is poultry.

71. The method or use of any one of clauses 56 to 70, wherein said subject is selected from the list consisting of chicken, turkey, quail, or pheasant.

72. The method or use of any one of clauses 56 to 71, wherein said subject is chicken.

73. The method or use of any one of clauses 56 to 72, wherein the immunogenic composition is administered once.

74. The method or use of any one of clauses 56 to 72, wherein the immunogenic composition is administered at two or more doses.

75. The method or use of any one of clauses 56 to 74, wherein said immunogenic composition is administered subcutaneously, intramuscularly, intracutaneously, oral or by eye drop.

76. The method or use of any one of clauses 56 to 75, wherein said immunogenic composition is administered subcutaneously intramuscularly.

77. The method or use of any one of clauses 56 to 76, wherein the immunogenic composition comprises $10^1$ to $10^5$ $EID_{50}$ per dose of the avian encephalomyelitis virus.

78. The method or use of any one of clauses 56 to 77, wherein the immunogenic composition comprises $10^1$ to $10^3$ $EID_{50}$ per dose of the avian encephalomyelitis virus.

79. The method or use of any one of clauses 56 to 78, wherein the immunogenic composition comprises $10^1$ to $10^5$ $EID_{50}$ per dose of the fowl pox virus.

80. The method or use of any one of clauses 56 to 79, wherein the immunogenic composition comprises $10^1$ to $10^3$ $EID_{50}$ per dose of the fowl pox virus.

81. The method or use of any one of clauses 56 to 80, wherein the immunogenic composition comprises $10^2$ to $10^{15}$ CFU per dose of the *avibacterium paragallinarum* before inactivation.

82. The method or use of any one of clauses 56 to 81, wherein the immunogenic composition comprises $10^5$ to $10^{10}$ CFU per dose of the *avibacterium paragallinarum* before inactivation.

83. The method of any one of clauses 56 to 82, wherein the immunogenic composition is administered to subjects from 2 weeks of age onwards, 3 weeks of age onwards, 4 weeks of age onwards, 6 weeks of age onwards or 8 weeks of age onwards.

84. The method of any one of clauses 56 to 83, wherein the immunogenic composition is administered to subjects from 3 weeks of age onwards.

85. The method of any one of clauses 56 to 84, wherein said method results in an improvement in an efficacy parameter selected from the group consisting of: shorter duration of bacteremia, shorter duration of viremia, a lower bacterial load, a lower viral load, reduced mortality, reduced tremors, reduced ataxia, reduced weakness, reduced weight loss, reduced drop in egg production, reduced lesions, reduced anorexia or combinations thereof, in comparison to a subject of a non-immunized control group of the same species.

86. An immunogenic composition comprising in combination:

a bacterin of *avibacterium paragallinarum*, and a modified live avian encephalomyelitis virus, and a modified live fowl pox virus; and a water-in-oil emulsion adjuvant or a water-in-oil emulsion adjuvant comprising a mineral oil.

87. An immunogenic composition comprising in combination:

a bacterin of *avibacterium paragallinarum* with $10^5$ to $10^{10}$ CFU per dose of the *avibacterium paragallinarum* before inactivation, and a modified live avian encephalomyelitis virus with $10^1$ to $10^3$ EIDso per dose of the avian encephalomyelitis virus, and a modified live fowl pox virus $10^1$ to $10^3$ $EID_{50}$ per dose of the fowl pox virus; and a water-in-oil emulsion adjuvant or a water-in-oil emulsion adjuvant comprising a mineral oil.

88. An immunogenic composition comprising in combination:

a bacterin of *avibacterium paragallinarum*, and a modified live avian encephalomyelitis virus, and a modified live fowl pox virus; and a water-in-oil emulsion adjuvant comprising a mineral oil comprising or consisting of saturated aliphatic and alicyclic hydrocarbons.

89. An immunogenic composition comprising in combination:
   a bacterin of *avibacterium paragallinarum* with $10^5$ to $10^{10}$ EID$_{50}$ per dose of the *avibacterium paragallinarum* before inactivation, and
   a modified live avian encephalomyelitis virus with $10^1$ to $10^3$ EID$_{50}$ per dose of the avian encephalomyelitis virus, and
   a modified live fowl pox virus $10^1$ to $10^3$ EID$_{50}$ per dose of the fowl pox virus; and
   a water-in-oil emulsion adjuvant comprising a mineral oil comprising or consisting of saturated aliphatic and alicyclic hydrocarbons.

90. The immunogenic composition of any one of clauses 86 to 89, wherein said immunogenic composition is a vaccine.

91. The immunogenic composition of any one of clauses 86 to 90, wherein said immunogenic composition comprises $10^2$ to $10^3$ EID$_{50}$ per dose of the avian encephalomyelitis virus.

92. The immunogenic composition of any one of clauses 86 to 91, wherein said immunogenic composition comprises $10^2$ to $10^3$ EID$_{50}$ per dose of the fowl pox virus.

93. The immunogenic composition of any one of clauses 86 to 92, wherein said immunogenic composition comprises $10^7$ to $10^9$ CFU per dose of the *avibacterium paragallinarum* before inactivation.

Method of Production

94. A method of preparing an immunogenic composition comprising:
a.) providing a bacterin of *avibacterium paragallinarum*; and
b.) providing a modified live avian encephalomyelitis virus; and
c.) providing a modified live fowl pox virus;
d.) combining the components of a) to c) to have a trivalent composition; and
e.) obtaining said trivalent composition; and
f.) addition of a pharmaceutically acceptable carrier.

95. The method of preparing the immunogenic composition of clause 94, wherein said pharmaceutically acceptable carrier is an adjuvant.

96. The method of preparing the immunogenic composition of clauses 94 or 95, wherein said pharmaceutically acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from *E. coli* (recombinant or otherwise), cholera toxin, IMS 1314, muramyl dipeptide, mineral oil, and combinations thereof.

97. The method of preparing the immunogenic composition of any one of clauses 94 to 96, wherein said pharmaceutically acceptable carrier is an adjuvant selected from the group consisting of mineral oil, water-in-oil emulsion, oil-in-water emulsion, water-in-oil-in-water emulsion, and combinations thereof.

98. The method of preparing the immunogenic composition of any one of clauses 94 to 97, wherein the immunogenic composition comprises $10^1$ to $10^5$ EID$_{50}$ per dose of the avian encephalomyelitis virus.

99. The method of preparing the immunogenic composition of any one of clauses 94 to 98, wherein the immunogenic composition comprises $10^1$ to $10^3$ EID$_{50}$ per dose of the avian encephalomyelitis virus.

100. The method of preparing the immunogenic composition of any one of clauses 94 to 99, wherein the immunogenic composition comprises $10^1$ to $10^5$ EID$_{50}$ per dose of the fowl pox virus.

101. The method of preparing the immunogenic composition of any one of clauses 94 to 100, wherein the immunogenic composition comprises $10^1$ to $10^3$ EID$_{50}$ per dose of the fowl pox virus.

102. The method of preparing the immunogenic composition any one of clauses 94 to 101, wherein the immunogenic composition comprises $10^2$ to $10^{15}$ CFU per dose of the *avibacterium paragallinarum* before inactivation.

103. The method of preparing the immunogenic composition of any one of clauses 94 to 102, wherein the immunogenic composition comprises $10^5$ to $10^{10}$ CFU per dose of the *avibacterium paragallinarum* before inactivation.

EXAMPLES

Figure 1:
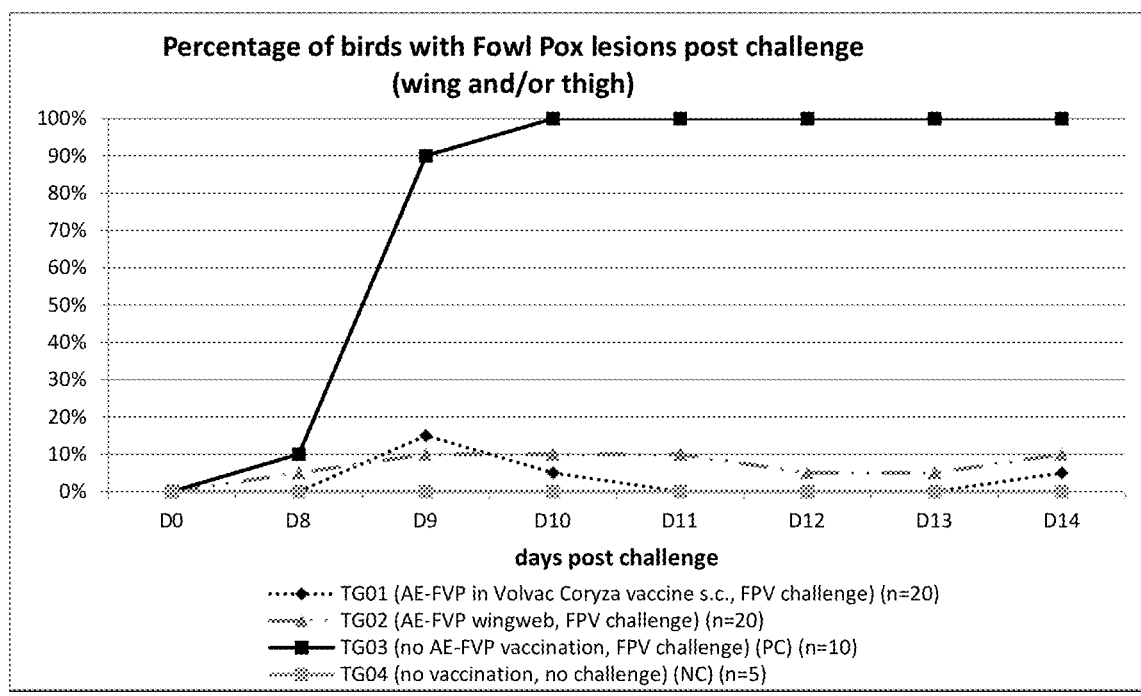
FIG. 1. Percentage of birds with pox lesions (on the wing and/or on the thigh) per day post challenge. PC=positive control; NC=negative control FIG. 2. Mean AE ELISA titer per Treatment Group. PC=positive control; NC=negative control

The following examples are set forth below to illustrate specific embodiments of the present invention. These examples are merely illustrative and are understood not to limit the scope or the underlying principles of the present invention.

Example 1

Determination of the Interference of a Vaccine Against Avian Infectious Coryza with the Efficacy of a Modified Live Vaccine Against Fowl Pox and Avian Encephalomyelitis in Poultry Study Objective Determination of the interference of an inactivated infectious avian coryza vaccine (*avibacterium paragallinarum*) with the efficacy of a live attenuated vaccine against fowl pox (FP) and a live attenuated vaccine against avian encephalomyelitis (AE) in poultry.

Experimental Design

For SPF-laying-type chickens (21 days of age at D0) are divided randomly into four Treatment Groups (TGs):
  TG01 (20 animals): vaccination with live AE-FP vaccine added to an inactivated coryza vaccine (triple vaccine) followed by a FP challenge. This group serves to detect interference of the coryza vaccine with the efficacy of the AE-FP vaccine.
  TG02 (20 animals): vaccination with live AE-FP vaccine (bivalent vaccine), followed by a FP challenge. This group serves to demonstrate the efficacy of the live AE-FP vaccine.
  TG03 (10 animals): not vaccinated but exposed to FP virus (FVP). This group serves to determine the challenge with FPV and thereby validate the animal trial (challenge control).
  TG04 (5 animals): not vaccinated but inoculated with sterile water. This group serves to control the absence of antibodies to AE and FPV and the absence of development of pox and the validity of the study.

The experimental unit was the Treatment Groups (TG).

The vaccinated animals receive one dose of the vaccines tested in the different combinations. The vaccination routes are the registered routes for the vaccines (table 1). Challenge is done three weeks after vaccination; TG01, TG02 and TG03 with a pathogenic pox strain through the wing web and the feather follicle method and TG04 (control group) is inoculated with sterile water. Thereafter and until the end of the study, the birds are observed daily and between days 29-35 are checked for the appearance of clinical signs due to fowl pox. At the end of the study, the birds are euthanized by inhalation of a $O_2$—$CO_2$ gas mixture. Blood samples are taken in all birds on days 0, 21 and 42. The blood is examined for the presence and absence of antibodies to AE.

TABLE 1

Experimental design of the study

| Treatment Group (TG) | No. of SPF layers | Vaccination | Blood sampling* D 0 | Check vaccinal pox D 8 | Pox challenge | Blood sampling** D 21 | Observation pox D 29-D 35 | Blood sampling** D 42*** |
|---|---|---|---|---|---|---|---|---|
| TG01 | 20 | Inactivated Coryza vaccine + Live AE + FP vaccine (subcutaneously) | Yes | Yes | Yes | Yes | Yes | Yes |
| TG02 | 20 | Live AE + FP vaccine (wing web) | Yes | Yes | Yes | Yes | Yes | Yes |
| TG03 | 10 | No | Yes | Yes | Yes | Yes | Yes | Yes |
| TG04 | 5 | No | Yes | Yes | No | Yes | Yes | Yes |

*For ELISA AE
**For ELISA AE
***Or earlier when bird is euthanized for animal welfare reasons The primary parameters in this study are:
1. the antibody response to the AE virus determined by using a standard commercially available ELISA test;
2. the determination of antibody titers to Coryza A using Hemagglutination Inhibition test;
3. the presence or absence of pox development at the inoculation sites (wing web and side of the thigh).

Materials and Methods

TABLE 2

Bivalent Vaccine against avian encephalomyelitis and fowl pox

| | |
|---|---|
| Generic name of active ingredient | Modified live virus vaccine against avian encephalomyelitis and fowl pox consisting of the Calnek 1733 strain of the AE virus and the Beaudette strain of FPV, originated in Specific Pathogen Free (SPF) chicken embryos. The product contains a minimum titer for AE: $10^{2.5}$ $EID_{50}$ and FP: $10^{2.5}$ $EID_{50}$ per dose. |
| Manufacturer | Boehringer Ingelheim Vetmedica |
| Storage conditions | 2 to 7° C. Protect from direct sunlight and do not freeze. |

TABLE 3

Trivalent Vaccine against avian infectious coryza and avian encephalomyelitis and fowl pox

| | |
|---|---|
| Generic name of active ingredient | Trivalent Inactivated water in oil vaccine against FP and AE (see table 2) and avian infectious coryza containing strains of *Avibacterium paragallinarum* of serogroups A, B and C; the minimum titer/dose/serotype: $10^{8.0}$CFU |
| Manufacturer | Boehringer Ingelheim Vetmedica |
| Storage conditions | 2 to 7° C. Protect from direct sunlight and do not freeze. |

TABLE 4

Challenge material

| | |
|---|---|
| Generic name of active ingredient | FPV |
| Manufacturer | GD (Gezondheidsdienst voor Dieren, Deventer, the Netherlands) |
| Potency | $10^{7.1}$ $EID_{50}$ per vial (1 mL) |
| Storage conditions | <−60° C. |

TABLE 5

Media

| | |
|---|---|
| Generic name of active ingredient | Sterile water |
| Manufacturer | GD |
| Storage conditions | 2-8° C. |

TABLE 6

Details of the vaccination and challenge procedure

| Treatment Group | No. of birds | Vaccine (D 0) | Dose | Route | Volume [mL] | Challenge (D 21) | n | Dose [$\log_{10}$ $EID_{50}$] | Route | Volume [mL] |
|---|---|---|---|---|---|---|---|---|---|---|
| TG01 | 20 | Inactivated infectious coryza with live AE + FP vaccine | 1 | s.c. | 0.5 | FPV | 20 | 4.1 | Wing web | 0.01 |
|  |  |  |  |  |  |  |  |  | feather follicles | 0.1 |
| TG02 | 20 | Live AE + FP vaccine | 1 | Wing web | 0.01 | FPV | 20 | 4.1 | Wing web | 0.01 |
|  |  |  |  |  |  |  |  |  | feather follicles | 0.1 |
| TG03 | 10 | — | — | — | — | FPV | 10 | 4.1 | Wing web | 0.01 |
|  |  |  |  |  |  |  |  |  | feather follicles | 0.1 |
| TG04 | 5 | — | — | — | — | Mock | 5 | — | Wing web | 0.01 |
|  |  |  |  |  |  |  |  |  | feather follicles | 0.1 |

TABLE 7

Adminstration of the Vaccine

| Dosing: | The inactivated infectious coryza vaccine and the live attenuated AE - FP vaccine is administered s.c. in a volume of 1 dose 0.5 mL once on D0. The live attenuated AE - FP vaccine alone is administered by the wing web method in a volume of 1 dose 0.01 mL once on D0. |
| Equipment for administering the Vaccine: | s.c.: A 1 ml sterile syringe will be used mounted with a 23Gx1" or equivalent needle wing web method: using a double needle for wing web application |
| Administration: | s.c.: dorsal side of the neck wing web method: double needle penetrates the skin fold of the wing | s.c. = subcutaneously

TABLE 8

Adminstration of the Challenge material

| Dosing: | $10^{4.1}$ $EID_{50}$ per chicken (see Administration) |
| Equipment: | Double needle for wing web Cotton swab for rubbing feather follicles |
| Administration: | $10^{4.1}$ $EID_{50}$ is administered on D21 by: dilute the stock of the challenge strain ($10^{7.1}$ $EID_{50}$) 1:100 in cold sterile, demineralized water to a titer of $10^{5.1}$ $EID_{50}$ per mL (=$10^{4.1}$ per 0.11 mL) intracutaneous administration according to the wing web method (double needle penetrates the skin fold of the wing): 1 dose of 0.01 mL per animal in this way is inoculated in one wing. feather follicle method: five feathers are pulled out on the side of the upper leg. Then, 0.1 mL poxvirus is rubbed gently at the feather follicles |

Observations

After challenge, the chickens are observed twice during the day for clinical signs. All signs and mortality are recorded and stored in the study file.

Sampling

Blood samples for serology are taken by puncturing the wing vein at days 0, 21 and 42. The blood is collected in serum-gel-tubes and let to clot for at least 2 hours at room temperature. Thereafter, serum is collected by centrifuging the tubes (4700 g; 10-15 minutes; room temperature) and aliquoted in double portions and stored at <−16° C. for further processing Hemagglutination Inhibition Test The presence of antibodies to Coryza serotype A was assessed in the sera of the birds taken at D42 using Hemagglutination Inhibition test using Kume strain A1 antigen. Twofold serial dilutions of sera were made in PBS, using round bottom microtiter plates. To each cup, equal amounts of hemagglutinating units (50 µl, 4 units) and 0.75% formalinized chicken erythrocytes (50 µl) were added. After incubation for 45 minutes at room temperature, the results were read as the maximum serum dilution that completely inhibited hemagglutination. Formalinized chicken erythrocytes were prepared by incubating chicken erythrocytes (washed twice in PBS) with PBS with 3% formaldehyde for 18 h at 4° C. Subsequently, the erythrocytes were washed once in PBS and suspended in PBS to make a 50% suspension which is diluted to 0.75% just before the test is done (Jacobs et al., 1992).

Results

A. Coryza A (*Avibacterium Paragallinarum*)

All birds of groups TG02, TG03 and TG04 that had not been vaccinated with the inactivated coryza vaccine had no detectable levels of antibodies against Coryza serotype A. This shows the high specificity of the test.

In group TG01 (live AE+FP added to inactivated coryza vaccine) antibody levels against Coryza serotype A were detected at expected levels (data not shown). These results show that there is no indication of a negative interference for the coryza vaccine component, what was expected. Any negative interference was predominantly expected for any or both of the live vaccine components.

B. Fowl Pox.

The result of the vaccination is shown in FIG. 1 (Percentage of birds with Fowl Pox lesions post challenge).

The study is valid because the negative control group (TG04) shows no pox lesions whereas the birds of the positive control group (TG03) all develop pox lesions. The same is concluded for the avian encephalitis part of the study as the non-vaccinated groups (TG03 and TG04) remain ELISA negative and both AE vaccinated groups (TG01 and TG02) become positive for AE antibodies.

The level of protection against pox for both groups vaccinated with the live attenuated AE-FP vaccine is shown in FIG. 1. All challenged non-vaccinated birds show pox lesions during a week or more; most of the vaccinated birds (approximately 75%) does not show any pox lesions post challenge; approximately 25% of the birds show minor lesions (lesions classified as small (size 2-3 mm)) for 1 to 3 days. The protection level in TG01 (inactivated coryza+AE-FP vaccines) is 96% and in TG02 (live AE-FP vaccine) is 92%, thus, protection level in TG01 is slightly higher. At 21 d. p. c., no lesions are present in both vaccinated groups whereas 89% of the birds of TG03 still show pox lesions.

These results show that there is, surprisingly, no indication of a negative interference by the inactivated coryza vaccine on the efficacy of the live attenuated FP vaccine. However, there is even a slightly positive synergistic effect for the pox vaccine efficacy in the triple vaccine combination which is surprising.

C. Avian Encephalomyelitis (AE) Virus

Figure 2:
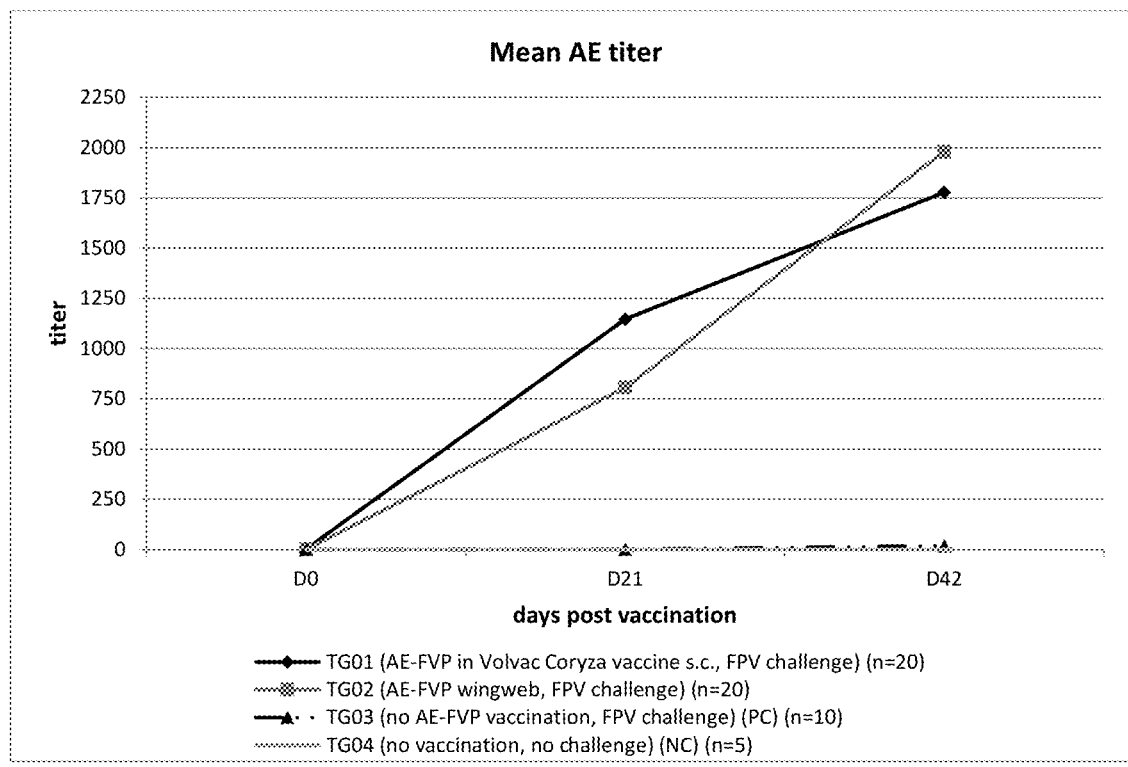

Table 9 and FIG. 2 show the mean AE ELISA titres for all groups on day of vaccination and at 21 and 42 d. p. v.

TABLE 9

Mean AE ELISA titer per Treatment Group

| TREATMENT GROUP | NUMBER OF BIRDS | VACCINATION D 0 | CHALLENGE STRAIN D 21 | MEAN AE ELISA TITER | | |
|---|---|---|---|---|---|---|
| | | | | D 0 | D 21 | D 42 |
| TG01 | 20 | Inactivated Coryza + live AE + FP vaccines | Fowl Pox Virus | 3 | 1146 | 1778 |
| TG02 | 20 | Live AE + FP vaccine | Fowl Pox Virus | 1 | 806 | 1980 |
| TG03 | 10 | — | Fowl Pox Virus | 0 | 1 | 19 |
| TG04 | 5 | — | — | 0 | 0 | 0 |

The mean titer development for the AE component is shown in FIG. 2. At 21 and 42 days post vaccination, the percentage of AE antibody ELISA positive birds of the group that had been vaccinated with the live attenuated AE-FP vaccine added to the inactivated coryza vaccine (TG01) is 81% and 95% respectively. The percentages of positives for the birds vaccinated with the live attenuated AE-Pox vaccine is respectively 57% and 90% on the same days (TG02). Thus, the percentage of antibody positive birds in TG01 is slightly higher. These results show that there is no indication of a negative interference by inactivated coryza vaccine on the efficacy of the live attenuated AE-FP vaccine. However, there is even a slightly positive synergistic effect for the AE vaccine efficacy (percentage of AE antibody positive birds is increased) in the triple vaccine combination which is surprising.

CONCLUSION

In summary, it can be concluded that there is no detectable interference with the efficacy of the live attenuated AE (avian encephalomyelitis) and FP (fowl pox) vaccine when added to the inactivated coryza vaccine (*avibacterium paragallinarum*). The data provided herein show that animals vaccinated with the triple vaccine are protected against fowl pox challenge and that animals produce high antibody titer against AE. There is even a slightly positive synergistic effect, for both the pox vaccine and AE vaccine efficacy, in the triple vaccine combination which is surprising. Often there is a negative effect expected on vaccine efficacy when combining vaccines to end up with a more complex vaccine composition in general. In particular, this would be expected when combining modified live vaccines with a bacterin comprising an adjuvant since the adjuvant may interfere with the activity of the modified live vaccine components.

The invention claimed is:

1. An immunogenic composition comprising: a) one or more antigens of a bacterin of *avibacterium paragallinarum* and one or more antigens of a modified live avian encephalomyelitis virus and one or more antigens of a modified live fowl pox virus; and b) a pharmaceutically acceptable carrier.

2. An immunogenic composition comprising: a) a bacterin of *avibacterium paragallinarum* and a modified live avian encephalomyelitis virus and a modified live fowl pox virus; and b) a pharmaceutically acceptable carrier.

3. The immunogenic composition of claim 1 or 2, wherein said immunogenic composition is a vaccine.

4. The immunogenic composition of claim 1 or 2, wherein said pharmaceutically acceptable carrier is an adjuvant.

5. The immunogenic composition of claim 1 or 2, wherein said pharmaceutically acceptable carrier is an adjuvant selected from the group consisting of mineral oil, water-in-oil emulsion, oil-in-water emulsion, water-in-oil-in-water emulsion, and combinations thereof.

6. A kit comprising the immunogenic composition of claim 1 or 2.

7. The kit according to claim 6, wherein the bacterin of *avibacterium paragallinarum*, the modified live avian encephalomyelitis virus and the modified live fowl pox virus are in one or two container(s).

8. A method for immunizing a subject comprising administering to such subject an immunogenic composition of claim 1 or 2.

9. A method of treating or preventing clinical signs caused by *avibacterium paragallinarum* and/or avian encephalomyelitis virus and/or fowl pox virus in a subject of need, the method comprising administering to the subject a therapeutically effective amount of an immunogenic composition according to claim 1 or 2.

10. A method of reducing the mortality and/or the tremors and/or the drop in egg production in a subject of need, in comparison to a subject of a non-immunized control group of the same species, the method comprising administering to the subject a therapeutically effective amount of an immunogenic composition according to claim 1 or 2.

11. The method of claim 8, wherein said subject is poultry.

12. The method of claim 8, wherein the immunogenic composition is administered once.

13. The method of claim 8, wherein said immunogenic composition is administered subcutaneously, intramuscularly, intracutaneously, oral or by eye drop.

14. The method of claim 8, wherein said method results in an improvement in an efficacy parameter selected from the group consisting shorter duration of bacteremia, shorter duration of viremia, a lower bacterial load, a lower viral load, reduced mortality, reduced tremors, reduced ataxia, reduced weakness, reduced weight loss, reduced drop in egg production, reduced lesions, reduced anorexia, reduced inflammation of infra orbital sinuses or combinations thereof, in comparison to a subject of a non-immunized control group of the same species.

\* \* \* \* \*